US006362326B1

(12) United States Patent
Sathe et al.

(10) Patent No.: US 6,362,326 B1
(45) Date of Patent: Mar. 26, 2002

(54) 11 CBY GENOMIC SEQUENCE

(75) Inventors: Ganesh Sathe, King of Prussia, PA (US); Catherine E. Ellis, Glassboro, NJ (US); Wendy Halsey, Kenneth Square; Derk Bergsma, Berwyn, both of PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/218,467

(22) Filed: Dec. 22, 1998

(51) Int. Cl.$^7$ .................. C07H 21/04; C07H 21/02; C12N 15/00; C12N 15/09; C12N 15/63

(52) U.S. Cl. .................. 536/23.5; 536/23.1; 435/320.1; 435/325; 435/455; 514/44

(58) Field of Search .................. 536/23.1, 23.5; 435/69.1, 252.3, 320.1, 325, 440, 455; 514/44

(56) References Cited

FOREIGN PATENT DOCUMENTS

EP 0 848 060 A2 6/1998 ........... C12N/15/12

OTHER PUBLICATIONS

Bergsma et al. GenCore Accession No. V28115, Sep. 1998.*
Kolakowski et al. GenCore Accession No. U71092, Apr. 1998.*
Cameron ER. Molecular Biotechnology. 7: 253–265, Jul. 1997.*
Leube et al. Journal of Cell Biology. 127(6): 1589–1601, Dec. 1994.*
Verma et al. Nature. 389: 239–242. Sep. 1997.*
Ledley FD. Pharmaceutical Research. 13: 1595–1613, Nov. 1996.*
Lakaye et al. Accession No. AF008650 and HSU71092, Jun. 1998.*
GenBank Accession No. T30384; Bergsma et al., Sep. 13, 1996 (first entry).
GenBank Accession No. Z86090; Lloyd, Submitted Jun. 4, 1999.

\* cited by examiner

*Primary Examiner*—Robert A. Schwartzman
*Assistant Examiner*—Peter Paras, Jr.
(74) *Attorney, Agent, or Firm*—William T. Han; Ratner & Prestia; William T. King

(57) ABSTRACT

The present invention relates to 11cby, in particular 11cby polypeptides and 11cby polynucleotides, recombinant materials and methods for their production. In another aspect, the invention relates to methods for using such polypeptides and polynucleotides, including the treatment of bacterial, fungal, protozoan and viral infections, particularly infection caused by HIV-1 or HIV-2; pain; cancers; diabetes; obesity; feeding and drinking abnormalities, such as anorexia and bulimia; asthma; Parkinson's disease; both acute and congestive heart failure; hypotension; hypertension; urinary retention; osteoporosis; angina pectoris; myocardial infarction; ulcers; allergies; benign prostatic hypertrophy and psychotic and neurological disorders, including anxiety, schizophrenia, manic depression, delirium, dementia or severe mental retardation, and dyskinesias, such as Huntington's disease or Gilles dela Tourett's syndrome, hereinafter referred to as "the Diseases", among others. In a still further aspect, the invention relates to diagnostic and prognostic assays for detecting diseases associated with inappropriate 11cby activity or levels. A method of performing genetic association studies for searching a disease susceptibility and/or drug response genes comprising using polymorphic markers in 11cby polynucleotides.

13 Claims, 6 Drawing Sheets

SEQ ID NO:1 (genomic sequence)

```
   1 GAGGTCCTGG CTATTGCCAG CATGGAGTGA CCTGTGTCAC CTCTGAGTGC
  51 CAGGCAAGGG TTCAGCAGCT GACGACTCAG CTTCTGCAGG ATGCTGGCAG
 101 CATAGCCAGC GAGATAGTTG GAAGCCGTCA GGGCACAGGG AAGGGGCCGA
 151 GGGTGCCCTG AGTGTGCATG GGGGCAGCC  CTGCTGCAGT CCAAGCCTTT
 201 GATTCCCAAG CTATGTGCAC AGTTTCCTCT GGACTCTGCC ATGTGGCCCA
 251 GCCACCCATA CCTGGAATAG GGCTAAGCC  AAGCTGCTCT CTCCTCCAAA
 301 GGGAGGCAGC CTGTGTGCTT TGTCCGTTTG CCTTTGCAGA GACCTCGATC
 351 CTCACGCAAG GCAAGCAGCA GCCCCTGTAA GCACACGAGA CAATCCCAAG
 401 TGTCAGTGGG AAGGAGATCC CTTTCCTGAT GGGGCTGCCT GTGTCCAGTC
 451 CCTCCCAGCT TCCCCAGGGC CTGGGGCTC  TGCAGGCATT CAGAAGTGGA
 501 AGCCAGCCAC AGCCTGGGAC TGAAGAGGTT AATGTGCATC TGCCTCCGAA
 551 TGTTAATGTG TCTAGGTGAT GTCAGTGGGA GCCATGAAGA AGGGAGTGGG
 601 GAGGGCAGTT GGGCTTGGAG GCGGCAGCGG CTGCCAGGCT ACGGAGGAAG
 651 ACCCCCTTCC CGACTGCGGG GCTTGCGCTC CGGGACAAGG TGGCAGGCGC
 701 TGGAGGCTGC CGCAGCCTGC GTGGGTGGAG GGGAGCTCAG CTCGGTTGTG
 751 GGAGCAGGCG ACCGGCACTG GCTGGATGGA CCTGGAAGCC TCGCTGCTGC
 801 CCACTGGTCC CAATGCCAGC AACACCTCTG ATGGCCCCGA TAACCTCACT
 851 TCGGCAGGTG AGTTGACTGG GAGCCCTCCC TCCTCTGGGC TGTGGGTGGA
 901 AAATGGGAAG GTTTCACCCC TGAGCCAAAC TGCTTGGGAA ACTTTATCAC
 951 AGTTCTTGGG GACAAGATCT GTGGTCTGCT TGCTCTGAG  GGGCAGGAGA
1001 AAAGGGGGCA ATGGTCCGCA GGGCAGACG  GGCAGGAGCA GAGCAGGGGG
1051 CGAAGGCATA TTCAGAATGG CAAGGAAGGG GGGCCAGCCG TGAGACAGCA
1101 GGGGAAGGCT CGCTGCTGGG TTCCAAAGAT GCTTGGCAGA AAAAATTCCA
1151 GGCTGGAAAA GCAAGCGAGA GAAGCTGGAG GGTGGTATGT GGGAGACAGC
1201 TGGGGGCTCA CTCCTGCACT GTTAGCCTCA GCTTTTTACT CCCACTTGGA
1251 TGATGAGGTC TGAGACATCC TTACTGCCAC CTGGGAGAGG CCCTGGGAAG
1301 GGAAGACTTC ACAGAGCCAT GAGGGGATTA ACTTTTCTGG TGAATTAAGC
1351 TTCCTGACAT TTCCAGAGCT GCGGTGCCCT GGGATTCCAG CTTTGAAGGA
1401 GAAAGGAAGG AAGGAAAAGA GGAAAGGCTT ATGTAGATAA TTTTTCCAGG
1451 CTGCTGAGCT CCAACAGACA GTTTCTGTCT CTGCTTCACT CAAGAAGCCC
1501 AGGCTCAGAA GATACCAATC AAGGAAATCC CCGCTAGGAA GCCTGGGGTA
1551 GGGAGAGCTG CTGGCTTGAC CAGGGCACAG CCGGCAAAAG CCTCTACAAG
1601 ACAGTCACCC ACAGATATGC CCAAGAATCA GTACACAGTT TCCAACCAGA
1651 GATCTCCAAA ATGAAACACT CAGGGCTACA CATAGGAAAA GCACGCACAC
1701 ACACACACAC ACACACACAG ACACTTACTT TTGTGTCCTT CTGGCTATGC
1751 TGACGAGTTT TCCTGGTGAA GCCCGGGGCT CACAGAGTAA TCTCTGCAGA
1801 CAACTGTGGT TCTTGCCTCT GGTGCCTGCA GGAGGCAGGC ATGTTGTGTC
1851 CTTCCAAGAC AGATGGCTCA GGGCACTCTG GTAGGATTCA CCAGGAAACT
1901 CATGGAGAAG GGAAAAGGGA CAAGATTAGC AACAGTGAAG GGAGGGAGAA
1951 TGGTGGGAGA GGATTCCAGA TGAACGGTGG GTCGCTGGAG GCTGAGCATG
2001 CCAGCAGGAT GTCAGTTCTC AGAGCAAAGC CCATGTCAAA CAGCCAACGC
2051 TTGCTCCTTC TGTCCCCAGG ATCACCTCCT CGCACGGGGA GCATCTCCTA
2101 CATCAACATC ATCATGCCTT CGGTGTTCGG CACCATCTGC CTCCTGGGCA
2151 TCATCGGGAA CTCCACGGTC ATCTTCGCGG TCGTGAAGAA GTCCAAGCTG
2201 CACTGGTGCA ACAACGTCCC CGACATCTTC ATCATCAACC TCTCGGTAGT
2251 AGATCTCCTC TTTCTCCTGG GCATGCCCTT CATGATCCAC CAGCTCATGG
```

Fig. 1

```
2301 GCAATGGGGT GTGGCACTTT GGGGAGACCA TGTGCACCCT CATCACGGCC
2351 ATGGATGCCA ATAGTCAGTT CACCAGCACC TACATCCTGA CCGCCATGGC
2401 CATTGACCGC TACCTGGCCA CTGTCCACCC CATCTCTTCC ACGAAGTTCC
2451 GGAAGCCCTC TGTGGCCACC CTGGTGATCT GCCTCCTGTG GGCCCTCTCC
2501 TTCATCAGCA TCACCCCTGT GTGGCTGTAT GCCAGACTCA TCCCCTTCCC
2551 AGGAGGTGCA GTGGGCTGCG GCATACGCCT GCCCAACCCA GACACTGACC
2601 TCTACTGGTT CACCCTGTAC CAGTTTTTCC TGGCCTTTGC CCTGCCTTTT
2651 GTGGTCATCA CAGCCGCATA CGTGAGGATC CTGCAGCGCA TGACGTCCTC
2701 AGTGGCCCCC GCCTCCCAGC GCAGCATCCG GCTGCGGACA AAGAGGGTGA
2751 CCCGCACAGC CATCGCCATC TGTCTGGTCT TCTTTGTGTG CTGGGCACCC
2801 TACTATGTGC TACAGCTGAC CCAGTTGTCC ATCAGCCGCC CGACCCTCAC
2851 CTTTGTCTAC TTATACAATG CGGCCATCAG CTTGGGCTAT GCCAACAGCT
2901 GCCTCAACCC CTTTGTGTAC ATCGTGCTCT GTGAGACGTT CCGCAAACGC
2951 TTGGTCCTGT CGGTGAAGCC TGCAGCCCAG GGGCAGCTTC GCGCTGTCAG
3001 CAACGCTCAG ACGGCTGACG AGGAGAGGAC AGAAAGCAAA GGCACCTGAT
3051 ACTTCCCCTG CCACCCTGCA CACCTCCAAG TCAGGGCACC ACAACACGCC
3101 ACCGGGAGAG ATGCTGAGAA AAACCCAAGA CCGCTCGGGA AATGCAGGAA
3151 GGCCGGGTTG TGAGGGGTTG TTGCAATGAA ATAAATACAT TCCATGGGGC
3201 TCACACGTTG CTGGGGAGGC CTGGAGTCAG GTTTGGGGTT TTCAGATATC
3251 AGAAATCCCC TTGGGGGAGC AGGATGAGAC CTTTGGATAG AACAGAAGCT
3301 GAGCAAGAGA ACATGTTGGT TTGGATAACC GGTTGCACTA TATCTGTGAG
3351 CTCTCAAATG TCTTCTTCCC AAGGCAAGAG GTGGAAGGGT ACTGACTGGG
3401 TTTGTTTAAA GTCAGGCAGG GCTGGAGTGA GCAGCCAGGG CCATGTTGCA
3451 CAAGGCCTGA GAGACGGGAA AGGGCCCGAT CGCTCTTT
```

SEQ ID NO:2 (amino acid sequence of 11cby protein)

```
  1 MDLEASLLPT GPNASNTSDG PDNLTSAGSP PRTGSISYIN IIMPSVFGTI
 51 CLLGIIGNST VIFAVVKKSK LHWCNNVPDI FIINLSVVDL LFLLGMPFMI
101 HQLMGNGVWH FGETMCTLIT AMDANSQFTS TYILTAMAID RYLATVHPIS
151 STKFRKPSVA TLVICLLWAL SFISITPVWL YARLIPFPGG AVGCGIRLPN
201 PDTDLYWFTL YQFFLAFALP FVVITAAYVR ILQRMTSSVA PASQRSIRLR
251 TKRVTRTAIA ICLVFFVCWA PYYVLQLTQL SISRPTLTFV YLYNAAISLG
301 YANSCLNPFV YIVLCETFRK RLVLSVKPAA QGQLRAVSNA QTADEERTES
351 KGT
```

Fig. 1 cont'd

SEQ ID NO:3 (5'-upstream sequence of the coding region)

```
  1 GAGGTCCTGG CTATTGCCAG CATGGAGTGA CCTGTGTCAC CTCTGAGTGC
 51 CAGGCAAGGG TTCAGCAGCT GACGACTCAG CTTCTGCAGG ATGCTGGCAG
101 CATAGCCAGC GAGATAGTTG AAGCCGTCA GGGCACAGGG AAGGGGCCGA
151 GGGTGCCCTG AGTGTGCATG GGGGGCAGCC CTGCTGCAGT CCAAGCCTTT
201 GATTCCCAAG CTATGTGCAC AGTTTCCTCT GGACTCTGCC ATGTGGCCCA
251 GCCACCCATA CCTGGAATAG GGCTAAGCC AAGCTGCTCT CTCCTCCAAA
301 GGGAGGCAGC CTGTGTGCTT TGTCCGTTTG CCTTTGCAGA GACCTCGATC
351 CTCACGCAAG GCAAGCAGCA GCCCTGTAA GCACACGAGA CAATCCCAAG
401 TGTCAGTGGG AAGGAGATCC CTTTCCTGAT GGGGCTGCCT GTGTCCAGTC
451 CCTCCCAGCT TCCCCAGGGC CTGGGGCTC TGCAGGCATT CAGAAGTGGA
501 AGCCAGCCAC AGCCTGGGAC TGAAGAGGTT AATGTGCATC TGCCTCCGAA
551 TGTTAATGTG TCTAGGTGAT GTCAGTGGGA GCCATGAAGA AGGGAGTGGG
601 GAGGGCAGTT GGGCTTGGAG GCGGCAGCGG CTGCCAGGCT ACGGAGGAAG
651 ACCCCCTTCC CGACTGCGGG GCTTGCGCTC CGGGACAAGG TGGCAGGCGC
701 TGGAGGCTGC CGCAGCCTGC GTGGGTGGAG GGAGCTCAG CTCGGTTGTG
751 GGAGCAGGCG ACCGGCACTG GCTGG
```

SEQ ID NO:4 (first coding sequence)

```
  1 ATGGACCTGG AAGCCTCGCT GCTGCCCACT GGTCCCAATG CCAGCAACAC
 51 CTCTGATGGC CCCGATAACC TCACTTCGGC AG
```

SEQ ID NO:5 (intron within the coding region)

```
  1 GTGAGTTGAC TGGGAGCCCT CCCTCCTCTG GGCTGTGGGT GGAAAATGGG
 51 AAGGTTTCAC CCCTGAGCCA AACTGCTTGG GAAACTTTAT CACAGTTCTT
101 GGGGACAAGA TCTGTGGTCT GCTTTGCTCT GAGGGGCAGG AGAAAAGGGG
151 GCAATGGTCC GCAGGGGCAG ACGGGCAGGA GCAGAGCAGG GGGCGAAGGC
201 ATATTCAGAA TGGCAAGGAA GGGGGGCCAG CCGTGAGACA GCAGGGGAAG
```

Fig. 1 cont'd

```
 251 GCTCGCTGCT GGGTTCCAAA GATGCTTGGC AGAAAAAATT CCAGGCTGGA
 301 AAAGCAAGCG AGAGAAGCTG GAGGGTGGTA TGTGGGAGAC AGCTGGGGGC
 351 TCACTCCTGC ACTGTTAGCC TCAGCTTTTT ACTCCCACTT GGATGATGAG
 401 GTCTGAGACA TCCTTACTGC CACCTGGGAG AGGCCCTGGG AAGGGAAGAC
 451 TTCACAGAGC CATGAGGGGA TTAACTTTTC TGGTGAATTA AGCTTCCTGA
 501 CATTTCCAGA GCTGCGGTGC CCTGGGATTC CAGCTTTGAA GGAGAAAGGA
 551 AGGAAGGAAA AGAGGAAAGG CTTATGTAGA TAATTTTTCC AGGCTGCTGA
 601 GCTCCAACAG ACAGTTTCTG TCTCTGCTTC ACTCAAGAAG CCCAGGCTCA
 651 GAAGATACCA ATCAAGGAAA TCCCCGCTAG AAGCCTGGG GTAGGGAGAG
 701 CTGCTGGCTT GACCAGGGCA CAGCCGGCAA AAGCCTCTAC AAGACAGTCA
 751 CCCACAGATA TGCCCAAGAA TCAGTACACA GTTTCCAACC AGAGATCTCC
 801 AAAATGAAAC ACTCAGGGCT ACACATAGGA AAAGCACGCA CACACACACA
 851 CACACACACA CAGACACTTA CTTTTGTGTC CTTCTGGCTA TGCTGACGAG
 901 TTTTCCTGGT GAAGCCCGGG GCTCACAGAG TAATCTCTGC AGACAACTGT
 951 GGTTCTTGCC TCTGGTGCCT GCAGGAGGCA GGCATGTTGT GTCCTTCCAA
1001 GACAGATGGC TCAGGCACT CTGGTAGGAT TCACCAGGAA ACTCATGGAG
1051 AAGGGAAAAG GGACAAGATT AGCAACAGTG AAGGGAGGGA GAATGGTGGG
1101 AGAGGATTCC AGATGAACGG TGGGTCGCTG GAGGCTGAGC ATGCCAGCAG
1151 GATGTCAGTT CTCAGAGCAA AGCCCATGTC AAACAGCCAA CGCTTGCTCC
1201 TTCTGTCCCC AG
```

Fig. 1 cont'd

SEQ ID NO:6 (second coding sequence)

```
  1 GATCACCTCC TCGCACGGGG AGCATCTCCT ACATCAACAT CATCATGCCT
 51 TCGGTGTTCG GCACCATCTG CCTCCTGGGC ATCATCGGGA ACTCCACGGT
101 CATCTTCGCG GTCGTGAAGA AGTCCAAGCT GCACTGGTGC AACAACGTCC
151 CCGACATCTT CATCATCAAC CTCTCGGTAG TAGATCTCCT CTTTCTCCTG
201 GGCATGCCCT TCATGATCCA CCAGCTCATG GGCAATGGGG TGTGGCACTT
251 TGGGGAGACC ATGTGCACCC TCATCACGGC CATGGATGCC AATAGTCAGT
301 TCACCAGCAC CTACATCCTG ACCGCCATGG CCATTGACCG CTACCTGGCC
351 ACTGTCCACC CCATCTCTTC CACGAAGTTC CGGAAGCCCT CTGTGGCCAC
401 CCTGGTGATC TGCCTCCTGT GGGCCCTCTC CTTCATCAGC ATCACCCCTG
451 TGTGGCTGTA TGCCAGACTC ATCCCCTTCC CAGGAGGTGC AGTGGGCTGC
501 GGCATACGCC TGCCCAACCC AGACACTGAC CTCTACTGGT TCACCCTGTA
551 CCAGTTTTTC CTGGCCTTTG CCCTGCCTTT TGTGGTCATC ACAGCCGCAT
601 ACGTGAGGAT CCTGCAGCGC ATGACGTCCT CAGTGGCCCC CGCCTCCCAG
651 CGCAGCATCC GGCTGCGGAC AAAGAGGGTG ACCCGCACAG CCATCGCCAT
701 CTGTCTGGTC TTCTTTGTGT GCTGGGCACC CTACTATGTG CTACAGCTGA
751 CCCAGTTGTC CATCAGCCGC CCGACCCTCA CCTTTGTCTA CTTATACAAT
801 GCGGCCATCA GCTTGGGCTA TGCCAACAGC TGCCTCAACC CCTTTGTGTA
851 CATCGTGCTC TGTGAGACGT TCCGCAAACG CTTGGTCCTG TCGGTGAAGC
901 CTGCAGCCCA GGGGCAGCTT CGCGCTGTCA GCAACGCTCA GACGGCTGAC
951 GAGGAGAGGA CAGAAAGCAA AGGCACCTGA
```

Fig. 1 cont'd

SEQ ID NO:7 (3'-sequence after the coding sequence)

```
  1 TACTTCCCCT GCCACCCTGC ACACCTCCAA GTCAGGGCAC CACAACACGC
 51 CACCGGGAGA GATGCTGAGA AAAACCCAAG ACCGCTCGGG AAATGCAGGA
101 AGGCCGGGTT GTGAGGGGTT GTTGCAATGA AATAAATACA TTCCATGGGG
151 CTCACACGTT GCTGGGGAGG CCTGGAGTCA GGTTTGGGGT TTTCAGATAT
201 CAGAAATCCC CTTGGGGGAG CAGGATGAGA CCTTTGGATA GAACAGAAGC
251 TGAGCAAGAG AACATGTTGG TTTGGATAAC CGGTTGCACT ATATCTGTGA
301 GCTCTCAAAT GTCTTCTTCC CAAGGCAAGA GGTGGAAGGG TACTGACTGG
351 GTTTGTTTAA AGTCAGGCAG GGCTGGAGTG AGCAGCCAGG GCCATGTTGC
401 ACAAGGCCTG AGAGACGGGA AAGGGCCCGA TCGCTCTTT
```

Fig. 1 cont'd

11 CBY GENOMIC SEQUENCE

FIELD OF THE INVENTION

This invention overall relates to the field of human genetics. More particularly, this invention relates to newly identified polypeptides and polynucleotides encoding such polypeptides, to the use of polynucleotides in gene therapy, and to production of such polypeptides and polynucleotides. In another aspect, this invention relates to prognostic and diagnostic methods for human diseases. This invention also relates to a method of performing genetic association studies for searching a disease susceptibility and/or drug response genes comprising using polymorphic markers. Yet in further aspect, the invention relates to transgenic animals, and use of transgenic animals for disease models to screening for therapeutic compounds.

BACKGROUND OF THE INVENTION

The drug discovery process is currently undergoing a fundamental revolution as it embraces 'functional genomics', that is, high throughput genome- or gene-based biology. This approach is rapidly superceding earlier approaches based on 'positional cloning'. A phenotype, that is a biological function or genetic disease, would be identified and this would then be tracked back to the responsible gene, based on its genetic map position.

Functional genomics relies heavily on the various tools of bioinformatics to identify gene sequences of potential interest from the many molecular biology databases now available. There is a continuing need to identify and characterise further genes and their related polypeptides/proteins, as targets for drug discovery.

It is well established that many medically significant biological processes are mediated by proteins participating in signal transduction pathways that involve G-proteins and/or second messengers, e.g., cAMP (Lefkowitz, Nature, 1991, 351:353–354). Herein these proteins are referred to as proteins participating in pathways with G-proteins or PPG proteins. Some examples of these proteins include the GPC receptors, such as those for adrenergic agents and dopamine (Kobilka, B. K., et al., Proc. Natl Acad. Sci., USA, 1987, 84:46–50; Kobilka, B. K., et al., Science, 1987, 238:650–656; Bunzow, J. R., et al., Nature, 1988, 336:783–787), G-proteins themselves, effector proteins, e.g., phospholipase C, adenyl cyclase, and phosphodiesterase, and actuator proteins, e.g., protein kinase A and protein kinase C (Simon, M. I., et al., Science, 1991, 252:802–8).

For example, in one form of signal transduction, the effect, of hormone binding is activation of the enzyme, adenylate cyclase, inside the cell. Enzyme activation by hormones is dependent on the presence of the nucleotide GTP. GTP also influences hormone binding. A G-protein connects the hormone receptor to adenylate cyclase. G-protein was shown to exchange GTP for bound GDP when activated by a hormone receptor. The GTP-carrying form then binds to activated adenylate cyclase. Hydrolysis of GTP to GDP, catalyzed by the G-protein itself, returns the G-protein to its basal, inactive form. Thus, the G-protein serves a dual role, as an intermediate that relays the signal from receptor to effector, and as a clock that controls the duration of the signal.

The membrane protein gene superfamily of G-protein coupled receptors has been characterized as having seven putative transmembrane domains. The domains are believed to represent transmembrane a-helices connected by extracellular or cytoplasmic loops. G-protein coupled receptors include a wide range of biologically active receptors, such as hormone, viral, growth factor and neuroreceptors.

G-protein coupled receptors (otherwise known as 7TM receptors) have been characterized as including these seven conserved hydrophobic stretches of about 20 to 30 amino acids, connecting at least eight divergent hydrophilic loops. The G-protein family of coupled receptors includes dopamine receptors which bind to neuroleptic drugs used for treating psychotic and neurological disorders. Other examples of members of this family include, but are not limited to, calcitonin, adrenergic, endothelin, cAMP, adenosine, muscarinic, acetylcholine, serotonin, histamine, thrombin, kinin, follicle stimulating hormone, opsins, endothelial differentiation gene-1, rhodopsins, odorant, and cytomegalovirus receptors. Most G-protein coupled receptors have single conserved cysteine residues in each of the first two extracellular loops which form disulfide bonds that are believed to stabilize functional protein structure. The 7 transmembrane regions are designated as TM1, TM2, TM3, TM4, TM5, TM6, and TM7. TM3 has been implicated in signal transduction. Phosphorylation and lipidation (palmitylation or farnesylation) of cysteine residues can influence signal transduction of some G-protein coupled receptors. Most G-protein coupled receptors contain potential phosphorylation sites within the third cytoplasmic loop and/or the carboxy terminus. For several G-protein coupled receptors, such as the b-adrenoreceptor, phosphorylation by protein kinase A and/or specific receptor kinases mediates receptor desensitization.

For some receptors, the ligand binding sites of G-protein coupled receptors are believed to comprise hydrophilic sockets formed by several G-protein coupled receptor transmembrane domains, said socket being surrounded by hydrophobic residues of the G-protein coupled receptors. The hydrophilic side of each G-protein coupled receptor transmembrane helix is postulated to face inward and form polar ligand binding site. TM3 has been implicated in several G-protein coupled receptors as having a ligand binding site, such as the TM3 aspartate residue. TM5 serines, a TM6 asparagine and TM6 or TM7 phenylalanines or tyrosines are also implicated in ligand binding.

G-protein coupled receptors can be intracellularly coupled by heterotrimeric G-proteins to various intracellular enzymes, ion channels and transporters (see, Johnson et al., Endoc. Rev., 1989, 10:317–331) Different G-protein a-subunits preferentially stimulate particular effectors to modulate various biological functions in a cell. Phosphorylation of cytoplasmic residues of G-protein coupled receptors have been identified as an important mechanism for the regulation of G-protein coupling of some G-protein coupled receptors. G-protein coupled receptors are found in numerous sites within a mammalian host.

Over the past 15 years, nearly 350 therapeutic agents targeting 7 transmembrane (7 TM) receptors have been successfully introduced onto the market.

SUMMARY OF THE INVENTION

The present invention relates to 11cby, in particular 11cby polypeptides and 11cby polynucleotides, recombinant materials and methods for their production. In another aspect, the invention relates to methods for using such polypeptides and polynucleotides, including the treatment of bacterial, fungal, protozoan and viral infections, particularly infection caused by HIV-1 or HIV-2; pain; cancers; diabetes; obesity; feeding and drinking abnormalities, such as anorexia and bulimia;

asthma; Parkinson's disease; both acute and congestive heart failure; hypotension; hypertension; urinary retention; osteoporosis; angina pectoris; myocardial infarction; ulcers; allergies; benign prostatic hypertrophy and psychotic and neurological disorders, including anxiety, schizophrenia, manic depression, delirium, dementia or severe mental retardation, and dyskinesias, such as Huntington's disease or Gilles dela Tourett's syndrome, hereinafter referred to as "the Diseases", amongst others. In a still further aspect, the invention relates to diagnostic and prognostic assays for detecting diseases associated with inappropriate 11cby activity or levels. A method of performing genetic association studies for searching a disease susceptibility and/or drug response genes comprising using polymorphic markers in 11cby polynucleotides is also subject of present invention. Further, the present invention relates to a method of providing an individual in need of 11cby polypeptide comprising providing a 11cby polynucleotide through a gene therapy. Yet in further aspect, the invention relates to transgenic animals, and use of transgenic animals for disease models to screening for therapeutic compounds.

BRIEF DESCRIPTION OF THE DRAWINGS

FIG. 1 is genomic sequence 11cby.

DESCRIPTION OF THE INVENTION

In a first aspect, the present invention relates to 11cby polynucleotides. Such polynucleotides include a polynucleotide comprising the polynucleotide of SEQ ID NO:1. The nucleotide sequence of SEQ ID NO:1 is a gDNA (genomic DNA) sequence containing a sequence which encode the polypeptide of the SEQ ID NO:2. Further 11cby polynucleotides of the present invention include isolated polynucleotides comprising a nucleotide sequence which has at least 70% identity, preferably at least 80% identity, more preferably at least 90% identity, yet more preferably at least 95% identity, to SEQ ID NO:1 over the entire length of SEQ ID NO:1. In this regard, polynucleotides which have at least 97% identity are highly preferred, whilst those with at least 98–99% identiy are more highly preferred, and those with at least 99% identity are most highly preferred. Such polynucleotides include a polynucleotide of SEQ ID NO:1.

The 11cby polynucleotides include a polynucleotide which hybridizes under stringent conditions to a polynucleotide of SEQ ID NO: 1 or to a fragment thereof, or to a complement of polynucleotide of SEQ ID NO:1 or to a fragment thereof.

The 11cby polynucleotides also include an isolated polynucleotide which comprises a polynucleotide which has at least (a) 70% identity;
(b) 80% identity;
(c) 90% identity;
(d) 95% identity;
(e) 97% identity; or
(f) 98% identity to a polynucleotide selected from the group consisting of
  a. SEQ ID NO:3;
  b. SEQ ID NO:5; and
  c. SEQ ID NO:7;
over the entire length of each SEQ ID NOS:3, 5 and 7, respectively.

The 11cby polynucleotides also include a polynucleotide which hybridizes under stringent conditions to any of the polynucleotide of SEQ ID NO: 3, 5 or 7, or to a fragment thereof, or to a complement to any of the polynucleotide of SEQ ID NO:3, 5 or 7, or to a fragment thereof.

The 11cby polynucleotides also include an isolated polynucleotide which has at least (a) 70% identity;
(b) 80% identity;
(c) 90% identity;
(d) 95% identity;
(e) 97% identity; or
(f) 98% identity to a polynucleotide selected from the group consisting of
  a. SEQ ID NO:4; and
  b. SEQ ID NO:6:
over the entire length of each SEQ ID NOS: 4 and 6, respectively.

The 11cby polynucleotides include a polynucleotide which hybridizes under stringent conditions to any of the polynucleotide of SEQ ID NO:4 or 6, or to a fragment thereof, or to a complement to any of the polynucleotide of SEQ ID NO:4 or 6, or to a fragment thereof.

A deposit containing a 11cby gDNA has been deposited with the American Type Culture Collection (ATCC), University Boulevard, Manassas, Va. 20110-2209, USA, on Oct. 29, 1998, and assigned ATCC Deposit Number 98964. The deposited material ATG-1222, hereinafter referred to as the "deposited clone" is DH10B containing pCYPAC1 that further contains the gDNA (genomic DNA). The nucleotide sequence of the polynucleotides contained in the deposited material, as well as the amino acid sequence of the polypeptide encoded thereby, are controlling in the event of any conflict with any description of sequences herein. The deposit has been made under the terms of the Budapest Treaty on the international recognition of the deposit of micro-organisms for purposes of patent procedure. The strain will be irrevocably and without restriction or condition released to the public upon the issuance of a patent. The deposit is provided merely as convenience to those of skill in the art and is not an admission that a deposit is required for enablement, such as that required under 35 U.S.C. §112.

In a further aspect, 11cby polynucleotides also include a polynculeotide which comprises a polynucleotide which has at least 70% identity, preferably, at least 80% identity, more preferably at least 90% identity, particularly at least 95% identity, to gDNA in the deposited clone over the entire length of the gDNA, as well as a nucleotide sequence comprising a fragment of such gDNA insert. Furthermore, those with at least 97% identity are highly preferred, those with at least 98–99% identity are most highly preferred, and those with at least 99% identity are most preferred.

The invention also provides polynucleotides which are complementary to all the aforementioned polynucleotides.

It will be readily appreciated that the deposited clone, or a fragment thereof, may also be used as a hybridization probe, for cDNA and genomic DNA, to isolate full-length cDNAs and genomic clones, as described elsewhere.

The 11cby polynucleotides also include polynucleotides which are complementary to all the above described polynucleotides.

In another aspect the present invention relates to 11cby polypeptides. 11cby polypeptides include polypeptides which are encoded by 11cby polynucleotides. Particular preferred member of the 11cby polypeptides is polypeptide of SEQ ID NO: 2. The polypeptide of SEQ ID NO: 2 is believed to be a member of the 7-transmembrane receptor family of polypeptides. It is therefore of interest because is has now been discovered to bind to 19 amino acid peptide melanin-concentrating hormone (MCH) with amino acid sequence of H-Asp-Phe-Asp-Met-Leu-Arg-Cys-Met-Leu-Gly-Arg-Val-Tyr-Arg-Pro-Cys-Trp-Gln-Val-OH. SEQ ID NO: 8. Its properties are hereinafter referred to as "11cby activity" or "11cby polypeptide activity" or "biological activity of 11cby". 11cby polypeptide and its encoding cDNA are descrbed in EP 0848060 published Jun. 17, 1998.

The polypeptides of the present invention may be in the form of the "mature" protein or may be a part of a larger protein such as a fusion protein. It is often advantageous to include an additional amino acid sequence which contains secretory or leader sequences, prosequences, sequences which aid in purification such as multiple histidine residues, or an additional sequence for stability during recombinant production.

The present invention also includes include variants of the aforementioned polypetides, that is polypeptides that vary from the referents by conservative amino acid substitutions, whereby a residue is substituted by another with like characteristics. Typical such substitutions are among Ala, Val, Leu and Ile; among Ser and Thr; among the acidic residues Asp and Glu; among Asn and Gln; and among the basic residues Lys and Arg; or aromatic residues Phe and Tyr. Particularly preferred are variants in which several, e.g. 1–5, 5–10, 10–20, 20–50, etc. amino acids are substituted, deleted, or added in any combination.

Polypeptides of the present invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

Preferred polypeptides and polynucleotides of the present invention are expected to have, inter alia, similar biological functions/properties to their homologous polypeptides and polynucleotides. Furthermore, preferred polypeptides and polynucleotides of the present invention have at least one 11cby activity.

Polynucleotides of the present invention may be obtained, using standard cloning and screening techniques, from a gDNA library derived from cells of human whole brain library. Polynucleotides of the invention can also be synthesized using well known and commercially available techniques.

When polynucleotides of the present invention are used for the recombinant production of polypeptides of the present invention, the polynucleotide may be the coding sequence for the mature polypeptide, by itself; or the coding sequence for the mature polypeptide in reading frame with other coding sequences, such as those encoding a leader or secretory sequence, a pre-, or pro- or prepro-protein sequence, or other fusion peptide portions. For example, a marker sequence which facilitates purification of the fused polypeptide can be encoded. In certain preferred embodiments of this aspect of the invention, the marker sequence is a hexa-histidine peptide, as provided in the pQE vector (Qiagen, Inc.) and described in Gentz et al., *Proc Natl Acad Sci USA* (1989) 86:821–824, or is an HA tag. The polynucleotide may also retain non-coding 5' and 3' sequences, such as transcribed, non-translated sequences, splicing and polyadenylation signals, ribosome binding sites and sequences that stabilize mRNA.

Further embodiments of the present invention include polynucleotides variants which comprise the polynucleotide of SEQ ID NO:1 in which 200 to 100, 100 to 50, 50 to 10, 5 to 10, 1 to 5, 1 to 3, 1 to 2 or 1, nucleotide residues are substituted, deleted or added, in any combination.

Polynucleotides which are identical or sufficiently identical to a nucleotide sequence contained in SEQ ID NO:1, may be used as hybridization probes for cDNA and genomic DNA, or as primers for a nucleic acid amplification (PCR) reaction, to isolate full-length cDNAs and genomic clones encoding polypeptides of the present invention, and to isolate cDNA and genomic clones of other genes (including genes encoding homologs, paralogs, and orthologs from species other than human) that have a high sequence similarity to SEQ ID NO:1. Typically these nucleotide sequences are 70% identical, preferably 80% identical, more preferably 90% identical, most preferably 95% identical to that of the referent. Even more preferably, they are 97–99% identical to the referent. The probes or primers will generally comprise at least 15 nucleotides, preferably, at least 30 nucleotides and may have at least 50 nucleotides. Particularly preferred probes will have between 30 and 50 nucleotides.

A polynucleotide encoding a polypeptide of the present invention, including homologs, paralogs, and orthologs from species other than human, may be obtained by a process which comprises the steps of screening an appropriate library under appropriate hybridization conditions altering for example, salt concentration, temperature, washing times and buffers with a labeled probe having the sequence of SEQ ID NO: 1 or a fragment thereof; and isolating full-length cDNA and genomic clones containing said polynucleotide sequence. Such hybridization techniques are well known to the skilled artisan. Preferred appropriate hybridization conditions are given for example in Chruch, G. M. and Gilbert, W (1984) Genomic sequencing. Proc. Natl. Acad. Sci. USA 81:1991–1995. One preferred condition includes overnight incubation at 42° C. in a solution comprising: 50% formamide, 5×SSC (150 mM NaCl, 15 mM trisodium citrate), 50 mM sodium phosphate (pH7.6), 5×Denhardt's solution, 10% dextran sulfate, and 20 microgram/ml denatured, sheared salmon sperm DNA; followed by washing the filters in 0.1×SSC at about 65° C. Thus the present invention also includes polynucleotides obtainable by screening an appropriate library under stingent hybridization conditions with a labeled probe having the sequence of SEQ ID NO:1 or a fragment thereof, or with a labeled probe having the complementary sequence to SEQ ID NO:1 or a fragment thereof.

Recombinant polypeptides of the present invention may be prepared by processes well known in the art from genetically engineered host cells comprising expression systems. Accordingly, in a further aspect, the present invention relates to expression systems which comprise a polynucleotide or polynucleotides of the present invention, to host cells which are genetically engineered with such expression sytems and to the production of polypeptides of the invention by recombinant techniques. Cell-free translation systems can also be employed to produce such proteins using RNAs derived from the DNA constructs of the present invention.

For recombinant production, host cells can be genetically engineered to incorporate expression systems comprising polynucleotides of the present invention or a portion thereof. Introduction of polynucleotides into host cells can be effected by methods described in many standard laboratory manuals, such as Davis et al., Basic Methods in Molecular Biology (1986) and Sambrook et al., Molecular Cloning: A Laboratory Manual, 2nd Ed., Cold Spring Harbor Laboratory Press, Cold Spring Harbor, N.Y. (1989). Preferred such methods include, for instance, calcium phosphate transfection, DEAE-dextran mediated transfection, transvection, microinjection, cationic lipid-mediated transfection, electroporation, transduction, scrape loading, ballistic introduction or infection.

Representative examples of appropriate hosts include bacterial cells, such as *streptococci, staphylococci, E. coli*, Streptomyces and *Bacillus subtilis* cells; fungal cells, such as yeast cells and Aspergillus cells; insect cells such as Drosophila S2 and Spodoptera Sf9 cells; animal cells such as CHO, COS, HeLa, C127, 3T3, BHK, HEK 293 and Bowes melanoma cells; and plant cells.

A great variety of expression systems can be used, for instance, chromosomal, episomal and virus-derived systems, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression systems may contain control regions that regulate as well as engender expression. Generally, any system or vector which is able to maintain, propagate or express a polynucleotide to produce a polypeptide in a host may be used. The appropriate nucleotide sequence may be inserted into an expression system by any of a variety of well-known and routine techniques, such as, for example, those set forth in Sambrook et al., *MOLECULAR CLONING, A LABORATORY MANUAL* (supra). Appropriate secretion signals may be incorporated into the desired polypeptide to allow secretion of the translated protein into the lumen of the endoplasmic reticulum, the periplasmic space or the extracellular environment. These signals may be endogenous to the polypeptide or they may be heterologous signals.

If a polypeptide of the present invention is to be expressed for use in agonist/antagonist screening assays, it is generally preferred that the polypeptide be produced at the surface of the cell. In this event, the cells may be harvested prior to use in the screening assay. If the polypeptide is secreted into the medium, the medium can be recovered in order to recover and purify the polypeptide. If produced intracellularly, the cells must first be lysed before the polypeptide is recovered.

Polypeptides of the present invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography is employed for purification. Well known techniques for refolding proteins may be employed to regenerate active conformation when the polypeptide is denatured during isolation and or purification.

The modem development of molecular biological techniques has permitted investigation into the genetic abnormalities that cause, or correlate with, specific human disease states and conditions. For example, restriction fragment length polymorphism (RFLP) analysis facilitates the identification of genetic defects which cause or are correlated with disease states, and facilitates the identification of individuals possessing the genetic defects. RFLP procedures involve digesting DNA with one or more restriction enzymes and analyzing the restriction fragments using, e.g., Southern blot hybridizations employing selected gene probes. See Alberts et al., Molecular Biology of the Cell, Second Edition, New York:Garland Publishing (1989), pp. 270–71.

The polymerase chain reaction (PCR) and its many variations are particularly useful tools for investigation into genetic abnormalities that underlie disease states and conditions. (See, e.g., Erlich et al., Current Communications in Molecular Biology: Polymerase Chain Reaction, Cold Spring Harbor:Cold Spring Harbor Press (1989); Innis et al., PCT Protocols: A Guide to Methods and Applications. San Diego:Academic Press (1990).) PCR is used to amplify a DNA or one or more portions thereof that are of particular interest, to facilitate further characterization of the amplified portion. Such further characterization includes gel electrophoresis to determine size, nucleotide sequencing, hybridization studies using particular probes, and the like. See generally, Sambrook et al., Molecular Cloning-A Laboratory Manual, Second Edition, Cold Spring Harbor:Cold Spring Harbor Press ( 1989).

This invention also relates to the use of polynucleotides of the present invention as diagnostic reagents. Individuals with the wild-type 11cby gene do not have Diseases which result from the 11cby allele. Detection of a mutated form of the gene will provide a diagnostic tool for a Disease, to prognose of a Disease, to determine the susceptibility to a Disease, to monitor a Disease progression, or to profile a Disease. As used herein a Disease refers to any of the Diseases defined earlier. Thus the present invention relates to a method of detecting variations in 11cby alleles among the population comprising comparing the 11cby gene sequences of the population. In further aspect, this invention also relates to a method of detecting a presence of or an absense of variation in a 11cby allele in an individual from that of SEQ ID NO: 1, comprising comparing a 11cby allele sequence of the individual with that of SEQ ID NO: 1.

In another aspect, the invention provides a method of screening an individual for an increased risk of developing a Disease comprising the steps of:

(a) assaying for a presence or absence of a 11cby polynucleotide mutation relative to 11cby polynucleotide in a normal individual; and (b) correlating the presence of a mutation to an increased risk of developing a Disease, and absence of mutation to no increased risk of developing a Disease.

Yet in another aspect, the invention provides a method for diagnosing a Disease in an individual comprising:

(a) assaying for a presence or absence of a 11cby polynucleotide mutation relative to 11cby polynucleotide in a normal individual; and (b) correlating the presence of a mutation to a presence of a Disease, and absence of mutation to an absence of a Disease.

Individuals carrying mutations in the gene may be detected at the DNA level by a variety of techniques. Nucleic acids for diagnosis may be obtained from, for example, a subject's cells, blood, urine, stool, sputum, hair, vaginal swabs, semen, saliva, tissue biopsy or autopsy material. Useful diagnostic techniques include, but are not limited to, fluorescent in situ hybridization (FISH), direct DNA sequencing, PFGE analysis (SSCA), RNase protection assay, allele-specific oligonucleotide (ASO), dot blot analysis and PCR-SSCP, denaturing HPLC as discussed in detail further below.

Direct DNA sequencing, either manual sequencing or automated fluorescent sequencing can detect sequence variation. Another approach is the single-stranded conformation polymorphism assay (SSCA or SSCP) (Orita et al., Proc. Natl. Acad. Sci. USA 86:2776–2770, 1989). This method does not detect all sequence changes, especially if the DNA fragment size is greater than 200 bp, but can be epitomized to detect most DNA sequence variation. The reduced detection sensitivity is a disadvantage, but the increased throughput possible with SSCA makes it an attractive, viable alternative to direct sequencing for mutation detection. The fragments which have shifted mobility on SSCA gels are then sequenced to determine the exact nature of the DNA sequence variation. Other approaches based on the detection of mismatches between the two complementary DNA strands include clamped denaturing gel electrophoresis (CDGE) (Sheffield, et al., Am. J. Hum. Genet. 49:699–706,1991), heteroduplex analysis (HA) (White et al., Genomics 12:301–306,1992) and chemical mismatch cleavage (CMC) (Grompe et al., Proc. Natl. Acad. Sci. USA 86:5855–5892,1989) Denaturing HPLC, similar to SSCP, can be used which uses a PCR amplified product, run down a heated HPLC column; the heating disassociates the DNA strands and one usually sees two peaks if there is a variation in the allelic forms. It works on the same principles as SSCP. Blind analysis of denaturing high-performance liquid chromatography as a tool for mutation detection. O'Donovan M C, Oefner P J, Roberts S C, Austin J, Hoogendoorn B, Guy C, Speight G, Upadhyaya M, Sommer S S, McGuffin P., Genomics Aug. 15, 1998; 52(1):44–9.

A rapid preliminary analysis to detect polymorphisms in DNA sequences can also be performed by looking at a series of Southern blots of DNA cut with one or more restriction enzymes, preferably with a large number of restriction enzymes. Each blot contains a series of normal individuals and a series of diseased cases, or both. Southern blots displaying hybridizing fragments differing in length from control DNA when probed with sequences near or including the 11cby locus indicate a possible mutation. If restriction enzymes which produce very large restriction fragments are used, then pulsed field gel electrophoresis (PFGE) is employed.

A review of currently available methods of detecting DNA sequence variation can be found in a recent review by Grompe (Grompe, Nature Genetics 5:111–117, 1993). Once a mutation is known, an allele specific detection approach such as allele specific oligonucleotide (ASO) hybridization can be utilized to rapidly screen large number of other samples for the same mutation. Among the most well known methods for confirming the presence of a susceptibility allele, are such as: 1) single stranded conformation analysis (SSCA) (Orita et al., Proc. Natl. Acad. Sci. USA 86:2776–2770, 1989); 2) denaturing gradient gel electrophoresis (DGGE) (Wartell et al., Nucl. Acids. Res. 18:2699–2705, 1990; Shieffield et al., Proc. Natl. Acad. Sci. USA 86:232–236, 1989); 3) RNase protection assays (Finkelstein et al., Genomics 7:167–172, 1990; Kinszler et al., Science 251:1366–1370,1991); 4) allele-specific oligonucleotides (ASOs) (Conner et al, Proc. Natl. Acad. Sci. USA 80:278–282, 1983); 5) the use of proteins which recognize nucleotide mismatches, such as the E. coli routs protein (Modrich, Ann. Rev. Genet. 25:229–253,1991); and 6) allele-specific PCR (Rano & Kidd, Nucl. Acids. Res. 17:8392, 1989). The present invention is not limited to a particular method but any and all methods which can be used to identity mutations.

In the first three methods (SSCA, DGGE and RNase protection assay), a new electrophoretic band appears. SSCA detects a band which migrates differentially because the sequence change causes a difference in single-strand, intermolecular base pairing. RNase protection involves cleavage of the mutant polynucleotide into two or more smaller fragments. DGGE detects differences in migration rates of mutant sequences compared to wild-type sequences, using a denaturing gradient gel. In an allele-specific oligonucleotide assay, an oligonucleotide is designed which detects a specific sequence, and the assay is performed by detecting a specific sequence, and the assay is performed by detecting the presence or absence of a hybridization signal. In the mutS assay, the protein binds only to sequences that contain a nucleotide mismatch in a heteroduplex between mutant and wild-type sequences.

Mismatches, according to the present invention, are hybridized nucleic acid duplexes in which the two strands are not 100% complementary. Lack of total homology may be due to deletion, insertions, inversions or substitutions. Mismatch detection can be used to detect point mutations in the gene. While these techniques are less sensitive than sequencing, they are simpler to perform on a large number of samples. An example of a mismatch cleavage technique is the RNase protection method. In the practice of the present invention, the method involves the use of a labeled riboprobe which is complementary to the human wild-type 11cby gene coding sequence. The riboprobe and either mRNA or DNA isolated from the sample are annealed (hybridized) together and subsequently digested with the enzyme RNase A which is able to detect some mismatches in a duplex RNA structure. A mismatch is detected by RNase A, it cleaves at the site of the mismatch. Thus, when the annealed RNA preparation is separated on an electrophoretic gel matrix, if a mismatch has been detected and cleaved by RNase A, an RNA product will be seen which is smaller than the full length duplex RNA for the riboprobe and the mRNA or DNA. The riboprobe need not be the full length of the 11cby mRNA or gene but can be a segment of either. If the riboprobe comprises only a segment of the 11cby mRNA or gene, it will be desirable to use a number of these probes to screen the whole mRNA sequence for mismatches.

In similar fashion, DNA probes can be used to detect mismatches, through enzymatic or chemical cleavage. See e.g., Cotton et al., Proc. Natl. Acad. Sci. USA 85:4397, 1988; Shenk et al., Proc. Natl. Acad. Sci. USA 72:989, 1975; Novack et al., Proc. Natl. Acad. Sci. USA 83:586, 1986. Alternatively, mismatches can be detected by shifts in the electrophoretic mobility of mismatched duplexes relative to matched duplexes. See, e.g., Cariello, Human Genetics 42:726, 1988. With either riboprobes or DNA probes, the cellular mRNA or DNA which might contain a mutation can be amplified using PCR before hybridization. Changes in DNA of the 11cby gene can also be detected using Southern hybridization, especially if the changes are gross rearrangements, such as deletions and insertions.

For allele-specific PCR, primers are used which hybridize at their 3' ends to a particular 11cby mutation. If the particular 11cby mutation is not present, an amplification product is not observed. Amplification Refractory Mutation System (ARMS) can also be used as disclosed in European Patent Application Publication No. 0332435 and in Newton et al. (Newton et al., Nucl. Acids Res. 17:2503–2516, 1989). By use of a battery of such allele-specific probes, PCR amplification products can be screened to identify the presence of a previously identified mutation in the 11cby gene.

The primer pairs can be made which are useful for determination of the nucleotide sequence of a particular 11cby allele using PCR. The pairs of single-stranded DNA primers can be annealed to sequences within or surrounding the 11cby gene on chromosome 22q13 in order to prime amplifying DNA synthesis of the 11cby gene itself. A complete set of these primers allows synthesis of all of the nucleotides of the 11cby gene coding sequences, i.e., the exons. The set of primers also preferably allows synthesis of both intron and exon sequences. As described above, allele-specific primers can also be used. Such primers anneal only to particular 11cby mutant alleles, and thus will only amplify a product in the presence of the mutant allele as a template.

In order to facilitate subsequent cloning of amplified sequences, primer may have restriction enzyme site sequences appended to their 5' ends. Thus, all nucleotides of the primers are derived from sequences within or adjacent to 11cby gene, except for the few nucleotides necessary to form a restriction enzyme site. Such enzymes and sites are well known in the art. The primers themselves can be synthesized using techniques which are well known in the art. Generally, the primers can be made using oligonucleotide synthesizing machines which are commercially available. Given the sequence shown in SEQ ID NO:1, design of particular primers is well within the skill of the art.

The nucleic acid probes/fragments provided by the present invention are useful for a number of purposes. They can be used in Southern hybridization to genomic DNA and in the RNase protection method for detecting point mutations already discussed above. The probes can be used to detect mismtaches with the 11cby gene or mRNA using other techniques. They can be used as probes in Northern blotting to detect the expression of the 11 cby gene product or in the probing of micrarrays of polynucleotides on a grid to look for related genes or as a member of such a grid to test for gene expression of many genes. Lockhart D J, Dong H, Byrne M C, Follettie M T, Gallo M V, Chee M S, Mittmann M, Wang C, Kobayashi M, Horton H, Brown EL *Expression monitoring by hybridization to high-density oligonucleotide arrays*. Nat Biotechnol 1996 December; 14(13):1675–80 Wodicka L, Dong H, Mittmann M, Ho M H, Lockhart D J *Genome-wide expression monitoring in Saccharomyces cerevisiae*. Nat Biotechnol 1997 December; 15(13):1359–67. Also they can be used to probe gene chip arrays looking for variants between individuals as a method for polymorphism discovery or diagnostically. Cronin M T, Fucini R V, Kim S M, Masino R S, Wespi R M, Miyada CG *Cystic fibrosis mutation detection by hybridization to light-generated DNA probe arrays*. Hum Mutat 1996;7(3):244–55.

The present invention also relates to genetic markers. Genetic markers are essential for linking a disease to a region of a chromosome. Such markers include restriction fragment length polymorphism (RFLPs) (Botstein et al., Am. J Hum. Genet. 32:314–331, 1980), markers with a variable number of tandem repeats (VNTRs) (Jeffreys et al., Nature, 314:67–73,1985; Nakamura et al., Science 235:1616–1622, 1987), and an abundant class of DNA polymorphisms on short tandem repeats (STRs), especially repeats of CpA (Weber and May, Am. J. Hum. Genet. 44:388–396, 1989; Litt et al., Am. J. Hum. Genet. 44:397–401, 1989) and single nucleotide polymorphisms (SNPs). Large-scale identification, mapping, and genotyping of single-nucleotide polymorphisms in the human genome, Wang D G, Fan J R, Siao C B, Berno A, Young P, Sapolsky R, Ghandour G, Perkins N, Winchester E, Spencer J, Kruglyak L, Stein L, Hsie L, Topaloglou T, Hubbell E, Robinson E, Mittmann M, Morris M S, Shen N, Kilburn D, Rioux J, Nusbaum C, Rozen S, Hudson T J, Lander E S, et al., Science May 15, 1998;280 (5366):1077–82. To generate a genetic map, one selects potential genetic markers and test them using DNA extracted from members of the kindreds being studied. The polynucleotide of SEQ ID NO: 1 may contain polymorphic markers, and are therefore suitable for genetic association studies searching for disease susceptibility and/or therapeutic (e.g. drug) response genes. Thus in another aspect, the invention provides a method of performing genetic association studies for searching a disease susceptibility genes or individual's likelihood of responding to a particular therapeutic intervention, comprising using polymorphic markers in the polynucleotide of SEQ ID NO: 1 and associating with a disease susceptibility genes or with likelihood of responding to a particular therapeutic intervention to the polymorphic markers.

In the present method, the phrase "screening a human subject for a risk of developing a Disease" means screening a human subject for the presence or absence of a genetic marker (i.e., a 11cby gene mutation), the presence of which correlates with an increased potential for developing the Disease. By "increased potential for developing a Disease" is meant a greater likelihood (probability) of developing the Disease than would otherwise be predicted (statistically), e.g. from the prevalence of the disorder in the general population or in the subject's ethnic population, the individual's age, sex, and the like. A person (e.g., a medical practitioner or other health care practitioner) can estimate a probability that any particular individual will develop a Disease through screening a human subject for a risk of developing a Disease.

In another aspect, the invention provides a kit for screening a human subject for an increased potential of developing a Disease, the kit comprising: an assay means for assaying a sample of genomic DNA from a human subject for the presence of an 11cby gene mutation, wherein the assay means produces a positive 11cby gene mutation assay result if 11cby gene mutation is present in the DNA of the subject, and the assay means produces a negative assay result if the DNA of the subject is free of the 11cby gene mutation; and a means for correlating a positive 11cby mutation assay result to an increased potential of developing a Disease.

Exemplary assay means include materials for performing molecular biological techniques to determine the presence of an 11cby gene mutation. Thus, the assay means may include DNA sequencing materials, PCR materials, restriction digestion/southern hybridization materials, and combinations thereof.

By a means for correlating a positive 11cby gene mutation assay result to an increased potential of developing a Disease is meant a chart, table, graph, text, or other reference that permits a medical practitioner to correlate assay results for a particular human subject to statistical risk for developing a particular Disease. For example, the chart, table, graph, or text is based on assay data disclosed herein, or upon further assay data obtained according to the teachings herein. The chart, table, graph, or text, or the data contained therein, may be provided in computer-readable form (e.g., on a floppy disc or compact disc).

Thus in another aspect, the present invention relates to a diagonostic kit which comprises:

(a) a polynucleotide of the present invention, preferably the nucleotide sequence of SEQ ID NO: 1, or a fragment thereof; or (b) a nucleotide sequence complementary to that of (a);

It will be appreciated that in any such kit, (a) or (b) may comprise a substantial component. Such a kit will be of use in diagnosing a disease or suspectability to a disease, particularly bacterial, fungal, protozoan and viral infections, particularly infection caused by HIV-1 or HIV-2; pain; cancers; diabetes; obesity; feeding and drinking abnormalities, such as anorexia and bulimia; asthma; Parkinson's disease; both acute and congestive heart failure; hypotension; hypertension; urinary retention; osteoporosis; angina pectoris; myocardial infarction; ulcers; allergies; benign prostatic hypertrophy and psychotic and neurological disorders, including anxiety, schizophrenia, manic depression, delirium, dementia or severe mental retardation, and dyskinesias, such as Huntington's disease or Gilles dela Tourett's syndrome, amongst others.

In a related aspect, the invention provides a genetic counseling method comprising the steps of: (a) isolating genomic DNA from a human individual; (b) assaying the DNA for a 11cby gene mutation relative to DNA of a normal human subject; (c) determining a potential for developing a Disease in the human individual, wherein the presence of the 11cby gene mutation in the genomic DNA of the human individual is indicative of an increased potential for developing the Disease; and (d) advising the human individual with respect to the individual's potential for developing the Disease. By "advising" the human individual is meant, e.g., providing the individual with the assay results and with the interpretation of those results (i.e., either normal or an increased potential for developing a Disease).

The nucleotide sequences of the present invention are also valuable for chromosome identification. The sequence is specifically targeted to, and can hybridize with, a particular location on an individual human chromosome. The mapping of relevant sequences to chromosomes according to the present invention is an important first step in correlating those sequences with gene associated disease. Once a sequence has been mapped to a precise chromosomal location, the physical position of the sequence on the chromosome can be correlated with genetic map data. Such data are found in, for example, V. McKusick, Mendelian Inheritance in Man (available on-line through Johns Hopkins University Welch Medical Library). The relationship between genes and diseases that have been mapped to the same chromosomal region are then identified through linkage analysis (coinheritance of physically adjacent genes) or direct detection of mutations in the gene itself.

The gene of the present invention maps to human chromosome 22q13. The chromosomal location which contains 11cby gene is called 11cby locus. An individual carries two homologous chromosomes, thus an individual possess two 11cby alleles.

Another aspect of the invention relates to a method for inducing an immunological response in a mammal which comprises inoculating the mammal with a polypeptide of the present invention, adequate to produce antibody and/or T cell immune response to protect said animal from the Diseases hereinbefore mentioned, amongst others. Yet another aspect of the invention relates to a method of inducing immunological response in a mammal which comprises, delivering a polypeptide of the present invention via a vector directing expression of the polynucleotide of the present invention and coding for the polypeptide in vivo in order to induce such an immunological response to produce antibody to protect said animal from Diseases.

In a further aspect, the present invention provides methods of treating abnormal conditions such as, for instance, bacterial, fungal, protozoan and viral infections, particularly infection caused by HIV-1 or HIV-2; pain; cancers; diabetes; obesity; feeding and drinking abnormalities, such as anorexia and bulimia; asthma; Parkinson's disease; both acute and congestive heart failure; hypotension; hypertension; urinary retention; osteoporosis; angina pectoris; myocardial infarction; ulcers; allergies; benign prostatic hypertrophy and psychotic and neurological disorders, including anxiety, schizophrenia, manic depression, delirium, dementia or severe mental retardation, and dyskinesias, such as Huntington's disease or Gilles dela Tourett's syndrome, related to either an excess of, or an under-expression of, 11cby polypeptide activity.

If the activity of the polypeptide is in excess, several approaches are available. One approach comprises inhibiting expression of the gene encoding endogenous 11cby polypeptide. Known such techniques involve the use of antisense sequences, either internally generated or separately administered (see, for example, O'Connor, *J Neurochem* (1991) 56:560 in Oligodeoxynucleotides as Antisense Inhibitors of Gene Expression, CRC Press, Boca Raton, Fla. (1988)). Alternatively, oligonucleotides which form triple helices with the gene can be supplied (see, for example, Lee et al., *Nucleic Acids Res* (1979) 6:3073; Cooney et al., *Science* (1988) 241:456; Dervan et al., *Science* (1991) 251:1360). These oligomers can be administered per se or the relevant oligomers can be expressed in vivo.

For treating abnormal conditions related to an under-expression of 11cby and its activity, several approaches are also available. One approach involves gene therapy to effect the endogenous production of 11cby by the relevant cells in the subject. More specifically, according to the present invention, a method is also provided of supplying wild-type 11cby gene function to a cell which carries mutant 11cby alleles. The wild-type 11cby gene or a part of the gene may be introduced into the cell in a vector such that the gene remains extrachromosomal. In such a situation, the gene will be expressed by the cell from the extrachromosomal location. More preferred is the situation where the wild-type 11cby gene or a part thereof is introduced into the mutant cell in such a way that it recombines with the endogenous mutant 11cby gene present in the cell. Such recombination requires a double recombination event which results in the correction of the 11cby gene mutation. Vectors for introduction of genes both for recombination and for extrachromosomal maintenance are know in the art, and any suitable vector may be used. Methods for introducing DNA into cells such as electroporation, calcium phosphate co-precipitation and viral transduction are known in the art, and the choice of method is within the competence of the routineer. Cells transformed with the wild-type 11cby gene can be used as model systems to study a Disease and drug treatments to treat the Disease.

As generally discussed above, the 11cby gene or fragment where applicable, may be employed in gene therapy methods in order to increase the amount of the expression products of such gene in cells in need thereof. Such gene therapy is particularly appropriate for use in cells in which wild type 11cby is under-expressed, and in which the level of 11cby polypeptide is absent or diminished compared to normal cells. It may also be useful to increase the level of expression of a given 11cby gene even in cells in which the mutant gene is expressed at a "normal" level, but the gene product is not fully functional.

Gene therapy would be carried out according to generally accepted methods, for example, as described by Friedman, T., In Therapy for Genetic Diseases, T. Frideman, ed., Oxford University Press, pp. 105–121, 1991. A virus or plasmid vector (see below), containing a copy of the 11cby gene linked to expression control elements and capable of replicating inside the cells, is prepared. Suitable vectors are known, such as disclosed in U.S. Pat. No. 5,252,479 and PCT published application WO 93/07282. The vector is then injected in the patient, either locally at the site of the cell, tissue or organ, in need thereof, or systemically. If the transfected gene is not permanently incorporated into the genome of each of the targeted cells, the treatment may have to be repeated periodically.

Gene transfer systems known in the art may be useful in the practice of the gene therapy methods of the present invention. These include viral and nonviral transfer methods. A number of viruses have been used as gene transfer vectors, including papovariuses, e.g., SV40 (Madzak et al., J. Gen. Virol, 73:1533–1536, 1992), adenovirus (Berkner, Curr. Top. Microbiol. Immunol., 158:39–61, 1992; Bernker et al., Bio Techniques 6:616–629, 1988; Gorziglia and Kapikian, J. Virol. 66:4407–4412, 1992; Quantin et al., Proc. Natl. Acad. Sci. USA 89:2851–2584, 1992; Rosenfeld et al., Cell 68:143–155, 1992; Wilkinson et al., Nucleic Acids Res. 20:2233–2239, 1992; Stratford-Perricaudet et al., Hum. Gene Ther. 1:241–256, 1990), vaccinia virus (Moss, Curr. Top. Microbiol. Immunol. 158:25–38, 1992) adenoassociated virus (Muzyczka, Curr. Top. Microbiol. Immunol. 158:97–123, 1992; Ohi et al., Gene 89:279–282, 1990), herpes viruses including HSV and EBV (Margolskee, Curr. Top. Microbiol. Immunol. 158:67–90, 1992; Johnson et al, J. Virol. 66: 2952–2965, 1992; Fink et al., Hum. Gene Ther. 3:11–19, 1992; Breakfield and Geller, Mol. Neurobiol. 1:337–371, 1987; Freese et al., Biochem. Pharmacol. 40:2189–2199, 1990), and retroviruses of avian (Brandyopadhyay and Temin, Mol. Cell. Biol. 4:749–754, 1984; Petropoulos et al., J. Virol. 66:3391–3397, 1992), murine (Miller, Curr. Top. Microbiol. Immunol. 158:1–24, 1992; Miller et al., Mol. Cell. Biol. 5:431–437, 1985; Sorge et al., Mol. Cell. Biol. 4:1730–1737, 1984; Mann and Baltimore, J. Virol. 54:401–407, 1985; Miller et al., J. Virol. 62:4337–4345, 1988, and human origin (Shimada et al., J. Clin. Invest. 88:1043–1047, 1991; Helseth et al., J. Virol. 64:2416–2420, 1990; Page et al., J. Virol. 64:5370–5276, 1990; Buchschacher and Panganiban, J. Virol. 66:2731–2739, 1992).

Nonviral gene transfer methods known in the art include chemical techniques such as calcium phosphate coprecipitation (Graham and van der EB., Virology 52: 456–467, 1973; Pellicer et al., Science 209:1414–1422, 1980); mechanical techniques, for example microinjection (Anderson et al., Proc. Natl. Acad. Sci. USA 77:5399–5403, 1980; Gordon et al., Proc. Natl. Acad. Sci. USA 77:7380–7384, 1980; Brinster et al., Cell 27:223–231, 1981; Constantini and Lacy, Nature 294:92–94, 1981); membrane fusion-mediated transfer via liposomes (Felgner et al., Proc. Natl. Acad. Sci. USA 84:7413–7417, 1987; Wang and Huang, Biochemistry 28:9508–9514, 1989; Kaneda et al., J. Biol. Chem. 264:12126–12129, 1989; Stewart et al., Hum. Gene Ther. 3:267–275, 1992; Nabel et al., Science 249:1285–1288, 1990); and direct DNA uptake and receptor-mediated DNA transfer (Wolff et al., Science 247:1465–1468, 1990; Wu et al., J. Biol. Chem. 266:14338–14342, 1991; Wagner et al., Proc. Natl. Acad. Sci. USA 87:3410–3414, 1990; Wagner et al., Proc. Natl. Acad. Sci. USA 88:4255–4259, 1991; Cotten et al., Proc. Natl. Acad. Sci. USA 87:4033–4037, 1990; Curiel et al., Proc. Natl. Acad. Sci. USA 88:8850–8854, 1991; Curiel et al., Hum. Gene Ther. 3:147–154, 1991). Viral-mediated gene transfer can be combined with direct in vivo gene transfer using liposome delivery, allowing one to direct the viral vectors to the tumor cells, if a Disease is tumor, and not into the surrounding nondividing cells. Alternatively, the retroviral vector produced cell line can be injected into tumors (Culver et al., Science, 256:1550–1552, 1992). Injection of producer cells would then provide a continuous source of vector particles.

In an approach which combines biological and physical gene transfer methods, plasmid DNA of any size is combined with a polylysine-conjugated antibody specific to the adenovirus hexon protein, and the resulting complex is bound to an adenovirus vector. The trimolecular complex is then used to infect cells. The adenovirus vector permits efficient binding, internalization, and degradation of the endosome before the coupled DNA is damaged.

Liposome/DNA complexes have been shown to be capable of mediating direct in vivo gene transfer. While in standard liposome preparations the gene transfer process is nonspecific, localized in vivo uptake and expression have been reported in tumor deposits, for example, following direct in situ administration (Nable, Hum. Gene Ther. 3:399–410, 1992).

Gene transfer techniques which target DNA directly to tissues in need thereof is preferred. Receptor-mediated gene transfer, for example, is accomplished by the conjugation of DNA (usually in the form of covalently closed supercoiled plasmid) to a protein ligand via polylysine. Ligands are chosen on the basis of the presence of the corresponding ligand receptors on the cell surface of the target cell/tissue type. One appropriate receptor/ligand pair may include, for example, the estrogen receptor and its ligand, estrogen (and estrogen analogues). These ligand-DNA conjugates can be injected directly into the blood if desired and are directed to the target tissue where receptor binding and internalization of the DNA-protein protein complex occurs. To overcome the problem of intracellular destruction of DNA, coinfection with adenovirus can be included to disrupt endosome function.

Also important is the development of experimental models of a Disease. Such models can be used to screen for agents that alter the progression of a Disease and to study pathological course of a Disease. Once a mutation causing a Disease is identified, it is possible using genetic manipulation to develop transgenic model systems and/or whole cell systems containing a mutated 11cby gene or a portion thereof. The model systems can be used for screening drugs and evaluating the efficacy of drugs in treating a Disease. In addition, these model systems provide a tool for defining the underlying biochemistry of 11cby polypeptide and its relationship to a Disease thereby providing a basis for rational drug design.

One type of cell system which can be used in the present invention can be naturally derived. For this, blood samples from an affected individual are obtained and permanently transformed into a lymphoblastoid cell line using, for example, Epstein-Barr virus. Once established, such cell lines can be grown continuously in suspension cultures and can be used in a variety of in vitro experiments to study 11cby expression and processing. Another cell line used in these studies comprises skin fibroblasts, derived from patients. Further cell cultures can be isolated form the transgenic animals or prepared from established cell cultures using the same constructs with standard cell transfection techniques.

A mutant 11cby gene of the present invention can be cloned and placed in a cloning vector. Examples of cloning vectors which can be used include, but are not limited to, Dcharon35, cosmid, or yeast artificial chromosome. Heterologous promoter sequences can also be used to control expression of 11cby coding sequences. The ability to regulate expression of the 11cby gene in transgenic animals is believed to be useful in evaluating the roles of the different 11cby gene products in a Disease. The ability to regulate expression of the 11cby gene in cultured cells is believed to be useful in evaluating expression and processing of the different 11cby gene products and may provide the basis for cell cultured drug screens. The metallothionine (MT) promoter is well characterized, has been employed in transgenic animals, and its expression can be regulated through modulation of zinc and glucocorticoid hormone levels (Palmiter et al., Nature 300, 611–615, 1982). Other alternatives for use in controlling human 11cby expression include, but are not limited to, the human S actin gene promoter (Ray et al., Genes and Development 5:2265–2273, 1991), the human platelet derived growth factor B (PDGFB) chain gene promoter (Sasahara et al., Cell 64:217–227, 1991), the rat sodium channel gene promoter (Maue et al, Neuron 4:223–231, 1990), the human copper-zinc superoxide dismutase gene promoter (Ceballos-Picot et al., Brain Res. 552:198–214, 1991), and promoters for members of the mammalian POU-domain regulatory gene family (Xi et al, Nature 340:35–42, 1989).

Large segments of human genomic DNA, when cloned into certain vectors, can be propagated as autonomously-replicating units in the yeast cell. Such vector-borne segments are referred to as yeast artificial chromosomes (YAC; Burke et al., Science 236:806 1987). A human YAC library is commercially available (Clonetech, Palo alto, Calif.). Other sources of YAC libraries can be obtained from a number of commercial or public sources including Research Genetics or genome Systems, UK Human Genome Resource Mapping Centre, libraries include the CEPH meaga YACs, the ICI YACs and the ICRF YACs with an average insert size of 250,000 base pairs (range of 180,000 to 500,000 base pairs). A YAC clone can be directly isolated by screening the library with the human 11cby cDNA. Other types of large insert libraries are also available in different vectors for example PACs and BACs these have average insert sizes of 100–120 000 base pairs. These can be obtained from commercial and public depositories including Research Genetics and Genome Systems. The inclusion of all of the essential gene regions in the clone can be confirmed by PCR analysis.

The YAC-11cby clone is established in embryonic stem (ES) cells by selecting for neomycin resistance encoded by the YAC vector. ES cells bearing the YAC-11cby clone are used to produce transgenic mice by established methods. The YAC-11cby gene bearing a mutation can be produced through the generation of a YAC library using genomic DNA from a person affected by a mutation. The clone is identified and established in ES cells as described above.

DNA molecules introduced into ES cells can also be integrated into the chromosome through the process of homologous recombination, described by Capecchi, MR in Science, 244:1288–1292 (1989).

The mutant 11cby gene can then be transferred to a host nonhuman animal such as a mouse. As a result of the transfer, the resultant transgenic nonhuman animal will preferably express one or more of the variant 11cby polypeptides.

Additional methods for producing transgenic animals are well known in the art.

Transgenic animals are used in the assessment of new therapeutic compositions, as exemplified by U.S. Pat. No. 5,223,610. These animals are also used in the development of predictive animal models for human disease states, as exemplified in U.S. Pat. No. 5,221,778. For example, transgenic animals are developed for assessing Alzheimer's disease (U.S. Pat. No. 7,769,626), multi-drug resistance to anticancer agents (U.S. Pat. No. 7,260,827), and carcinogenic substances (U.S. Pat. No. 4,736,866). Therefore, the mutated genes of the present invention which are believed to cause a Disease in Chromosome 22q13-linked pedigrees provide a useful means for developing transgenic animals to assess this Disease.

Transgenic animal technology also offers a whole animal expression-cloning system in which introduced genes are expressed to give large amounts of 11cby polypeptide of the present invention. Thus in one aspect the invention relates to a transgenic animal comprising a 11cby polynucleotide.

Polynucleotide and polypeptide sequences form a valuable information resource with which to identify further sequences of similar homology. This is most easily facilitated by storing the sequence in a computer readable medium and then using the stored data to search a sequence database using well known searching tools, such as GCC. Accordingly, in a further aspect, the present invention provides for a computer readable medium having stored thereon a polynucleotide comprising the sequence of SEQ ID NO:1 and/or a polypeptide sequence encoded thereby.

The following definitions are provided to facilitate understanding of certain terms used frequently hereinbefore.

"Isolated" means altered "by the hand of man" from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide separated from the coexisting materials of its natural state is "isolated", as the term is employed herein.

"Polynucleotide" generally refers to any polyribonucleotide or polydeoxribonucleotide, which may be unmodified RNA or DNA or modified RNA or DNA. "Polynucleotides" include, without limitation, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term "polynucleotide" also includes DNAs or RNAs containing one or more modified bases and DNAs or RNAs with backbones modified for stability or for other reasons. "Modified" bases include, for example, tritylated bases and unusual bases such as inosine. A variety of modifications may be made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as post-translational processing, or by chemical modification techniques which are well known in the art. Such modifications are well described in basic texts and in more detailed monographs, as well as in a voluminous research literature. Modifications may occur anywhere in a polypeptide, including the peptide backbone, the amino acid side-chains and the amino or carboxyl termini. It will be appreciated that the same type of modification may be present to the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from post-translation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination (see, for instance, PROTEINS— STRUCTURE AND MOLECULAR PROPERTIES, 2nd Ed., T. E. Creighton, W. H. Freeman and Company, New York, 1993; Wold, F., Post-translational Protein Modifications: Perspectives and Prospects, pgs. 1–12 in POST-TRANSLATIONAL COVALENT MODIFICATION OF PROTEINS, B. C. Johnson, Ed., Academic Press, New York, 1983; Seifter et al., "Analysis for protein modifications and nonprotein cofactors", Meth Enzymol (1990) 182:626–646 and Rattan et al., "Protein Synthesis: Post-translational Modifications and Aging", Ann NY Acad Sci (1992) 663:48–62).

"Variant" refers to a polynucleotide or polypeptide that differs from a reference polynucleotide or polypeptide, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations or chromosomal translocations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis.

"Identity," as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48: 1073 (1988). Preferred methods to determine identity are designed to give the largest match between the sequences tested. Methods to determine identity and similarity are codified in publicly available computer programs. Preferred computer program methods to determine identity and similarity between two sequences include, but are not limited to, the GCG program package (Devereux, J., et al., Nucleic Acids Research 12(1): 387 (1984)), BLASTP, BLASTN, and FASTA (Atschul, S. F. et al., J. Molec. Biol. 215: 403–410 (1990). The BLAST X program is publicly available from NCBI and other sources (BLAST Manual, Altschul, S., et al., NCBI NLM NIH Bethesda, Md. 20894; Altschul, S., et al., J. Mol. Biol. 215: 403–410 (1990). The well known Smith Waterman algorithm may also be used to determine identity.

Preferred parameters for polypeptide sequence comparison include the following:
1) Algorithm: Needleman and Wunsch, J. Mol Biol. 48: 443–453 (1970) Comparison matrix: BLOSSUM62 from Hentikoff and Hentikoff, Proc. Natl. Acad. Sci. USA. 89:10915–10919 (1992)
Gap Penalty: 12
Gap Length Penalty: 4

A program useful with these parameters is publicly available as the "gap" program from Genetics Computer Group, Madison Wis. The aforementioned parameters are the default parameters for peptide comparisons (along with no penalty for end gaps).

Preferred parameters for polynucleotide comparison include the following:
1) Algorithm: Needleman and Wunsch, J. Mol Biol. 48: 443–453 (1970)
Comparison matrix: matches=+10, mismatch=0
Gap Penalty: 50
Gap Length Penalty: 3
Available as: The "gap" program from Genetics Computer Group, Madison Wis. These are the default parameters for nucleic acid comparisons.

By way of example, a polynucleotide sequence of the present invention may be identical to the reference sequence of SEQ ID NO: 1, that is be 100% identical, or it may include up to a certain integer number of nucleotide alterations as compared to the reference sequence. Such alterations are selected from the group consisting of at least one nucleotide deletion, substitution, including transition and transversion, or insertion, and wherein said alterations may occur at the 5' or 3' terminal positions of the reference nucleotide sequence or anywhere between those terminal positions, interspersed either individually among the nucleotides in the reference sequence or in one or more contiguous groups within the reference sequence. The number of nucleotide alterations is determined by multiplying the total number of nucleotides in SEQ ID NO:1 by the numerical percent of the respective percent identity(divided by 100) and subtracting that product from said total number of nucleotides in SEQ ID NO:1, or:

$$n_n \leq x_n - (x_n \cdot Y),$$

wherein $n_n$ is the number of nucleotide alterations, $x_n$ is the total number of nucleotides in SEQ ID NO:1, and y is, for instance, 0.70 for 70%, 0.80 for 80%, 0.85 for 85%, 0.90 for 90%, 0.95 for 95%, etc., and wherein any non-integer product of $x_n$ and y is rounded down to the nearest integer prior to subtracting it from $x_n$. Alterations of a polynucleotide sequence encoding the polypeptide of SEQ ID NO:2 may create nonsense, missense or frameshift mutations in this coding sequence and thereby alter the polypeptide encoded by the polynucleotide following such alterations.

"Fusion protein" refers to a protein encoded by two, often unrelated, fused genes or fragments thereof. In one example, EP-A-0 464 discloses fusion proteins comprising various portions of constant region of immunoglobulin molecules together with another human protein or part thereof. In many cases, employing an immunoglobulin Fc region as a part of a fusion protein is advantageous for use in therapy and diagnosis resulting in, for example, improved pharmacokinetic properties [see, e.g., EP-A 0232 262]. On the other hand, for some uses it would be desirable to be able to delete the Fc part after the fusion protein has been expressed, detected and purified.

All publications, including but not limited to patents and patent applications, cited in this specification are herein incorporated by reference as if each individual publication were specifically and individually indicated to be incorporated by reference herein as though fully set forth.

What is claimed is:

1. An isolated polynucleotide consisting of a nucleotide sequence which is at least 70% identical to the nucleotide sequence of SEQ ID NO:1 over the entire length of SEQ ID NO:1, wherein the polypeptide encoded by said isolated polynucleotide has the ability to bind melanin-concentrating hormone.

2. An expression vector comprising a polynucleotide of claim 1, wherein said polynucleotide is operably linked to cis-acting control elements that direct expression of said polynucleotide in a host cell.

3. A process for producing a recombinant host cell comprising transforming a host cell in vitro with the expression vector of claim 2.

4. A recombinant host cell produced by the process of claim 3.

5. A process for producing a polypeptide comprising culturing a recombinant host cell of claim 4 under conditions sufficient for the production of said polypeptide and recovering said polypeptide from the culture.

6. An isolated polynucleotide comprising the nucleotide sequence of SEQ ID NO: 1, wherein the polypeptide encoded by said isolated polynucleotide has the ability to bind melanin-concentrating hormone.

7. An isolated polynucleotide consisting of the nucleotide sequence of SEQ ID NO:1.

8. An isolated polynucleotide consisting of a nucleotide sequence selected from the group consisting of:
  (a) the nucleotide sequence of SEQ ID NO:3;
  (b) the nucleotide sequence of SEQ ID NO:5; and
  (c) the nucleotide sequence of SEQ ID NO:7.

9. An isolated polynucleotide consisting of a nucleotide sequence selected from the group consisting of:
  (a) the nucleotide sequence of SEQ ID NO:4; and
  (b) the nucleotide sequence of SEQ ID NO:6.

10. A polynucleotide which is fully complementary to any of the polynucleotides of claims 1 to 9.

11. A method of detecting a presence of or an absence of variation in a 11 cby allele in an individual from that of SEQ ID NO: 1, comprising comparing a 11 cby allele sequence of the individual with that of SEQ ID NO: 1.

12. A method of claim 11 which further comprises isolating DNA from said individual.

13. An isolated polynucleotide consisting of a nucleotide sequence which is at least 70% identical to a genomic (g) DNA contained in ATCC Deposit number 98964 over the entire length of said gDNA, wherein the polypeptide encoded by said isolated polynucleotide has the ability to bind melanin-concentrating hormone.

* * * * *

SEQUENCE LISTING

<160> NUMBER OF SEQ ID NOS: 8

<210> SEQ ID NO 1
<211> LENGTH: 3488
<212> TYPE: DNA
<213> ORGANISM: HOMO SAPIENS

<400> SEQUENCE: 1

```
gaggtcctgg ctattgccag catggagtga cctgtgtcac ctctgagtgc caggcaaggg      60
ttcagcagct gacgactcag cttctgcagg atgctggcag catagccagc gagatagttg     120
gaagccgtca gggcacaggg aaggggccga gggtgccctg agtgtgcatg gggggcagcc     180
ctgctgcagt ccaagccttt gattcccaag ctatgtgcac agtttcctct ggactctgcc     240
atgtggccca gccacccata cctggaatag gggctaagcc aagctgctct ctcctccaaa     300
gggaggcagc ctgtgtgctt tgtccgtttg cctttgcaga gacctcgatc ctcacgcaag     360
gcaagcagca gccctgtaa gcacacgaga caatcccaag tgtcagtggg aaggagatcc     420
ctttcctgat ggggctgcct gtgtccagtc cctcccagct tccccagggc cctggggctc     480
tgcaggcatt cagaagtgga agccagccac agcctgggac tgaagaggtt aatgtgcatc     540
tgcctccgaa tgttaatgtg tctaggtgat gtcagtggga gccatgaaga agggagtggg     600
gagggcagtt gggcttggag gcggcagcgg ctgccaggct acggaggaag accccttcc     660 cgactgcggg gcttgcgctc cgggacaagg tggcaggcgc tggaggctgc cgcagcctgc     720
gtgggtggag gggagctcag ctcggttgtg ggagcaggcg accggcactg gctggatgga     780
cctggaagcc tcgctgctgc ccactggtcc caatgccagc aacacctctg atggccccga     840
taacctcact tcggcaggtg agttgactgg gagccctccc tcctctgggc tgtgggtgga     900
aaatgggaag gtttcacccc tgagccaaac tgcttgggaa actttatcac agttcttggg     960
gacaagatct gtggtctgct ttgctctgag gggcaggaga aaaggggca atggtccgca    1020 ggggcagacg ggcaggagca gagcagggg cgaaggcata ttcagaatgg caaggaaggg    1080
gggccagccg tgagacagca ggggaaggct cgctgctggg ttccaaagat gcttggcaga    1140
aaaaattcca ggctggaaaa gcaagcgaga gaagctggag ggtggtatgt gggagacagc    1200
tgggggctca ctcctgcact gttagcctca gcttttttact cccacttgga tgatgaggtc    1260
tgagacatcc ttactgccac ctgggagagg ccctgggaag ggaagacttc acagagccat    1320 gagggggatta acttttctgg tgaattaagc ttcctgacat ttccagagct gcggtgccct    1380
gggattccag ctttgaagga gaaggaagg aaggaaaaga ggaaaggctt atgtagataa    1440
tttttccagg ctgctgagct ccaacagaca gtttctgtct ctgcttcact caagaagccc    1500
aggctcagaa gataccaatc aaggaaatcc ccgctaggaa gcctggggta gggagagctg    1560
```

```
ctggcttgac cagggcacag ccggcaaaag cctctacaag acagtcaccc acagatatgc    1620
ccaagaatca gtacacagtt tccaaccaga gatctccaaa atgaaacact cagggctaca    1680
cataggaaaa gcacgcacac acacacacac acacacacag acacttactt ttgtgtcctt    1740
ctggctatgc tgacgagttt tcctggtgaa gcccggggct cacagagtaa tctctgcaga    1800
caactgtggt tcttgcctct ggtgcctgca ggaggcagga tgttgtgtc cttccaagac    1860 agatggctca gggcactctg gtaggattca ccaggaaact catggagaag gaaaaggga    1920 caagattagc aacagtgaag ggagggagaa tggtgggaga ggattccaga tgaacggtgg    1980
gtcgctggag gctgagcatg ccagcaggat gtcagttctc agagcaaagc ccatgtcaaa    2040
cagccaacgc ttgctccttc tgtccccagg atcacctcct cgcacgggga gcatctccta    2100
catcaacatc atcatgcctt cggtgttcgg caccatctgc ctcctgggca tcatcgggaa    2160
ctccacggtc atcttcgcgg tcgtgaagaa gtccaagctg cactggtgca caacgtccc    2220 cgacatcttc atcatcaacc tctcggtagt agatctcctc tttctcctgg gcatgccctt    2280
catgatccac cagctcatgg gcaatggggt gtggcacttt ggggagacca tgtgcaccct    2340
catcacggcc atggatgcca atagtcagtt caccagcacc tacatcctga ccgccatggc    2400
cattgaccgc tacctggcca ctgtccaccc catctcttcc acgaagttcc ggaagccctc    2460
tgtggccacc ctggtgatct gcctcctgtg ggccctctcc ttcatcagca tcaccctgt    2520 gtggctgtat gccagactca tccccttccc aggaggtgca gtgggctgcg catacgcct    2580 gcccaaccca gacactgacc tctactggtt caccctgtac cagttttttcc tggcctttgc    2640 cctgccttttt gtggtcatca cagccgcata cgtgaggatc ctgcagcgca tgacgtcctc    2700
agtggccccc gcctcccagc gcagcatccg gctgcggaca aagagggtga cccgcacagc    2760
catcgccatc tgtctggtct tctttgtgtg ctgggcaccc tactatgtgc tacagctgac    2820
ccagttgtcc atcagccgcc cgaccctcac ctttgtctac ttatacaatg cggccatcag    2880
cttgggctat gccaacagct gcctcaaccc ctttgtgtac atcgtgctct gtgagacgtt    2940
ccgcaaacgc ttggtcctgt cggtgaagcc tgcagcccag gggcagcttc gcgctgtcag    3000
caacgctcag acggctgacg aggagaggac agaaagcaaa ggcacctgat acttcccctg    3060
ccaccctgca cacctccaag tcagggcacc acaacacgcc accgggagag atgctgagaa    3120
aaacccaaga ccgctcggga aatgcaggaa ggccgggttg tgaggggttg ttgcaatgaa    3180
ataaatacat tccatggggc tcacacgttg ctggggaggc ctggagtcag gtttggggtt    3240
ttcagatatc agaaatcccc ttgggggagc aggatgagac cttggatag aacagaagct    3300 gagcaagaga acatgttggt ttggataacc ggttgcacta tatctgtgag ctctcaaatg    3360
tcttcttccc aaggcaagag gtggaagggt actgactggg tttgtttaaa gtcaggcagg    3420
gctggagtga gcagccaggg ccatgttgca caaggcctga gagacgggaa agggcccgat    3480
cgctctttt                                                           3488
```

<210> SEQ ID NO 2
<211> LENGTH: 353
<212> TYPE: PRT
<213> ORGANISM: HOMO SAPIENS

<400> SEQUENCE: 2

Met Asp Leu Glu Ala Ser Leu Leu Pro Thr Gly Pro Asn Ala Ser Asn
1               5                   10                  15

Thr Ser Asp Gly Pro Asp Asn Leu Thr Ser Ala Gly Ser Pro Pro Arg

```
            20                  25                  30
Thr Gly Ser Ile Ser Tyr Ile Asn Ile Ile Met Pro Ser Val Phe Gly
            35                  40                  45

Thr Ile Cys Leu Leu Gly Ile Ile Gly Asn Ser Thr Val Ile Phe Ala
 50                  55                  60

Val Val Lys Lys Ser Lys Leu His Trp Cys Asn Asn Val Pro Asp Ile
 65                  70                  75                  80

Phe Ile Ile Asn Leu Ser Val Val Asp Leu Leu Phe Leu Leu Gly Met
                85                  90                  95

Pro Phe Met Ile His Gln Leu Met Gly Asn Gly Val Trp His Phe Gly
                100                 105                 110

Glu Thr Met Cys Thr Leu Ile Thr Ala Met Asp Ala Asn Ser Gln Phe
                115                 120                 125

Thr Ser Thr Tyr Ile Leu Thr Ala Met Ala Ile Asp Arg Tyr Leu Ala
130                 135                 140

Thr Val His Pro Ile Ser Ser Thr Lys Phe Arg Lys Pro Ser Val Ala
145                 150                 155                 160

Thr Leu Val Ile Cys Leu Leu Trp Ala Leu Ser Phe Ile Ser Ile Thr
                165                 170                 175

Pro Val Trp Leu Tyr Ala Arg Leu Ile Pro Phe Pro Gly Gly Ala Val
                180                 185                 190

Gly Cys Gly Ile Arg Leu Pro Asn Pro Asp Thr Asp Leu Tyr Trp Phe
                195                 200                 205

Thr Leu Tyr Gln Phe Phe Leu Ala Phe Ala Leu Pro Phe Val Val Ile
210                 215                 220

Thr Ala Ala Tyr Val Arg Ile Leu Gln Arg Met Thr Ser Ser Val Ala
225                 230                 235                 240

Pro Ala Ser Gln Arg Ser Ile Arg Leu Arg Thr Lys Arg Val Thr Arg
                245                 250                 255

Thr Ala Ile Ala Ile Cys Leu Val Phe Phe Val Cys Trp Ala Pro Tyr
                260                 265                 270

Tyr Val Leu Gln Leu Thr Gln Leu Ser Ile Ser Arg Pro Thr Leu Thr
                275                 280                 285

Phe Val Tyr Leu Tyr Asn Ala Ala Ile Ser Leu Gly Tyr Ala Asn Ser
                290                 295                 300

Cys Leu Asn Pro Phe Val Tyr Ile Val Leu Cys Glu Thr Phe Arg Lys
305                 310                 315                 320

Arg Leu Val Leu Ser Val Lys Pro Ala Ala Gln Gly Gln Leu Arg Ala
                325                 330                 335

Val Ser Asn Ala Gln Thr Ala Asp Glu Glu Arg Thr Glu Ser Lys Gly
                340                 345                 350

Thr
```

<210> SEQ ID NO 3
<211> LENGTH: 775
<212> TYPE: DNA
<213> ORGANISM: HOMO SAPIENS

<400> SEQUENCE: 3

```
gaggtcctgg ctattgccag catggagtga cctgtgtcac ctctgagtgc caggcaaggg      60
ttcagcagct gacgactcag cttctgcagg atgctggcag catagccagc gagatagttg     120
gaagccgtca gggcacaggg aaggggccga gggtgccctg agtgtgcatg ggggcagcc      180
ctgctgcagt ccaagccttt gattcccaag ctatgtgcac agtttcctct ggactctgcc     240
```

-continued

```
atgtggccca gccacccata cctggaatag gggctaagcc aagctgctct ctcctccaaa    300
gggaggcagc ctgtgtgctt tgtccgtttg cctttgcaga gacctcgatc ctcacgcaag    360
gcaagcagca gcccctgtaa gcacacgaga caatcccaag tgtcagtggg aaggagatcc    420 cttcctgat ggggctgcct gtgtccagtc cctcccagct tccccagggc ctggggctc      480 tgcaggcatt cagaagtgga agccagccac agcctggac tgaagaggtt aatgtgcatc     540
tgcctccgaa tgttaatgtg tctaggtgat gtcagtggga ccatgaaga agggagtggg    600 gagggcagtt gggcttggag gcggcagcgg ctgccaggct acgaggaag accccctccc     660 cgactgcggg gcttgcgctc cgggacaagg tggcaggcgc tggaggctgc cgcagcctgc    720
gtgggtggag gggagctcag ctcggttgtg ggagcaggcg accggcactg gctgg         775
```

<210> SEQ ID NO 4
<211> LENGTH: 82
<212> TYPE: DNA
<213> ORGANISM: HOMO SAPIENS

<400> SEQUENCE: 4

```
atggacctgg aagcctcgct gctgcccact ggtcccaatg ccagcaacac ctctgatggc     60
cccgataacc tcacttcggc ag                                             82
```

<210> SEQ ID NO 5
<211> LENGTH: 1212
<212> TYPE: DNA
<213> ORGANISM: HOMO SAPIENS

<400> SEQUENCE: 5

```
gtgagttgac tgggagccct ccctcctctg gctgtgggt ggaaaatggg aaggtttcac      60
ccctgagcca aactgcttgg gaaactttat cacagttctt ggggacaaga tctgtggtct    120
gctttgctct gaggggcagg agaaaagggg gcaatggtcc gcaggggcag acgggcagga   180
gcagagcagg gggcgaaggc atattcagaa tggcaaggaa ggggggccag ccgtgagaca    240 gcagggaag gctcgctgct gggttccaaa gatgcttggc agaaaaaatt ccaggctgga     300
aaagcaagcg agagaagctg gagggtggta tgtgggagac agctgggggc tcactcctgc    360
actgttagcc tcagcttttt actcccactt ggatgatgag gtctgagaca tccttactgc    420
cacctgggag aggccctggg aagggaagac ttcacagagc catgagggga ttaacttttc    480
tggtgaatta agcttcctga catttccaga gctgcggtgc cctgggattc cagctttgaa    540
ggagaaagga aggaaggaaa agaggaaagg cttatgtaga taattttttcc aggctgctga   600 gctccaacag acagtttctg tctctgcttc actcaagaag cccaggctca gaagatacca    660
atcaaggaaa tccccgctag gaagcctggg gtagggagag ctgctggctt gaccagggca    720
cagccggcaa aagcctctac aagacagtca cccacagata tgcccaagaa tcagtacaca    780
gtttccaacc agagatctcc aaaatgaaac actcagggct acacatagga aaagcacgca    840
cacacacaca cacacacaca cagacactta cttttgtgtc cttctggcta tgctgacgag    900
ttttcctggt gaagcccggg gctcacagag taatctctgc agacaactgt ggttcttgcc    960
tctggtgcct gcaggaggca ggcatgttgt gtccttccaa gacagatggc tcagggcact   1020
ctggtaggat tcaccaggaa actcatggag aagggaaaag ggacaagatt agcaacagtg   1080
aagggaggga gaatggtggg agaggattcc agatgaacgg tgggtcgctg gaggctgagc   1140
atgccagcag gatgtcagtt ctcagagcaa agcccatgtc aaacagccaa cgcttgctcc   1200
``` ttctgtccccag                                                                                    1212

<210> SEQ ID NO 6
<211> LENGTH: 980
<212> TYPE: DNA
<213> ORGANISM: HOMO SAPIENS

<400> SEQUENCE: 6

| gatcacctcc | tcgcacgggg | agcatctcct | acatcaacat | catcatgcct | tcggtgttcg | 60 |
| gcaccatctg | cctcctgggc | atcatcggga | actccacggt | catcttcgcg | gtcgtgaaga | 120 |
| agtccaagct | gcactggtgc | aacaacgtcc | ccgacatctt | catcatcaac | ctctcggtag | 180 |
| tagatctcct | ctttctcctg | ggcatgccct | tcatgatcca | ccagctcatg | ggcaatgggg | 240 |
| tgtggcactt | tggggagacc | atgtgcaccc | tcatcacggc | catggatgcc | aatagtcagt | 300 |
| tcaccagcac | ctacatcctg | accgccatgg | ccattgaccg | ctacctggcc | actgtccacc | 360 |
| ccatctcttc | cacgaagttc | cggaagccct | ctgtggccac | cctggtgatc | tgcctcctgt | 420 |
| gggccctctc | cttcatcagc | atcacccctg | tgtggctgta | tgccagactc | atccccttcc | 480 |
| caggaggtgc | agtgggctgc | ggcatacgcc | tgcccaaccc | agacactgac | ctctactggt | 540 |
| tcaccctgta | ccagttttc  | ctggcctttg | ccctgccttt | tgtggtcatc | acagccgcat | 600 |
| acgtgaggat | cctgcagcgc | atgacgtcct | cagtggcccc | cgcctcccag | cgcagcatcc | 660 |
| ggctgcggac | aaagagggtg | acccgcacag | ccatcgccat | ctgtctggtc | ttctttgtgt | 720 |
| gctgggcacc | ctactatgtg | ctacagctga | cccagttgtc | catcagccgc | ccgaccctca | 780 |
| cctttgtcta | cttatacaat | gcggccatca | gcttgggcta | tgccaacagc | tgcctcaacc | 840 |
| cctttgtgta | catcgtgctc | tgtgagacgt | tccgcaaacg | cttggtcctg | tcggtgaagc | 900 |
| ctgcagccca | gggcagctt  | cgcgctgtca | gcaacgctca | gacggctgac | gaggagagga | 960 |
| cagaaagcaa | aggcacctga | | | | | 980 |

<210> SEQ ID NO 7
<211> LENGTH: 439
<212> TYPE: DNA
<213> ORGANISM: HOMO SAPIENS

<400> SEQUENCE: 7

| tacttcccct | gccaccctgc | acacctccaa | gtcagggcac | acaacacgc  | caccgggaga | 60 |
| gatgctgaga | aaacccaag  | accgctcggg | aaatgcagga | aggccgggtt | gtgagggtt  | 120 |
| gttgcaatga | aataaataca | ttccatgggg | ctcacacgtt | gctggggagg | cctggagtca | 180 |
| ggtttgggt  | tttcagatat | cagaaatccc | cttgggggag | caggatgaga | cctttggata | 240 |
| gaacagaagc | tgagcaagag | aacatgttgg | tttggataac | cggttgcact | atatctgtga | 300 |
| gctctcaaat | gtcttcttcc | caaggcaaga | ggtggaaggg | tactgactgg | gtttgtttaa | 360 |
| agtcaggcag | ggctggagtg | agcagccagg | gccatgttgc | acaaggcctg | agagacggga | 420 |
| aagggcccga | tcgctctttt | | | | | 439 |

<210> SEQ ID NO 8
<211> LENGTH: 21
<212> TYPE: PRT
<213> ORGANISM: HOMO SAPIENS

<400> SEQUENCE: 8

```
-continued

His Asp Phe Asp Met Leu Arg Cys Met Leu Gly Arg Val Tyr Arg Pro
 1               5                  10                  15

Cys Trp Gln Val His
                20
```